(12) United States Patent
Gillespie et al.

(10) Patent No.: US 7,758,548 B2
(45) Date of Patent: Jul. 20, 2010

(54) COUPLING FOR AN AUTO-INJECTION DEVICE

(75) Inventors: Richard David Gillespie, Athens, TX (US); Doug Owen Crow, Ben Wheeler, TX (US)

(73) Assignee: West Pharmaceutical Services of Delaware, Inc., Lionville, PA (US)

( * ) Notice: Subject to any disclaimer, the term of this patent is extended or adjusted under 35 U.S.C. 154(b) by 501 days.

(21) Appl. No.: 11/297,225

(22) Filed: Dec. 8, 2005

(65) Prior Publication Data

US 2006/0178629 A1  Aug. 10, 2006

Related U.S. Application Data

(60) Provisional application No. 60/634,486, filed on Dec. 9, 2004.

(51) Int. Cl.
*A61M 5/20* (2006.01)

(52) U.S. Cl. .................................................. 604/134

(58) Field of Classification Search ................. 604/110, 604/131, 134, 135, 136, 137, 138, 156
See application file for complete search history.

(56) References Cited

U.S. PATENT DOCUMENTS

| | | | |
|---|---|---|---|
| 2,561,233 A | 7/1951 | Ryan et al. |
| 3,306,290 A | 2/1967 | Weltman |
| 3,572,336 A | 3/1971 | Hershberg |
| 3,705,582 A | 12/1972 | Stumpf et al. |
| 3,707,968 A | 1/1973 | Koenig |
| 3,708,089 A | 1/1973 | Holder et al. |
| 3,834,387 A | 9/1974 | Brown |
| 3,901,402 A | 8/1975 | Ayres |
| 4,059,109 A | 11/1977 | Tischlinger |
| 4,445,895 A | 5/1984 | Margulies |
| 4,542,749 A | 9/1985 | Caselgrandi et al. |
| 4,581,016 A | 4/1986 | Gettig |
| D286,164 S | 10/1986 | Tinz |
| D287,603 S | 1/1987 | Bruhn |
| 4,643,721 A | 2/1987 | Brunet |

(Continued)

FOREIGN PATENT DOCUMENTS

CN 1011761 A 6/1987

(Continued)

OTHER PUBLICATIONS

International Search Report and Written Opinion for related International Patent Application No. PCT/US08/52427; mailed Aug. 4, 2008.

(Continued)

*Primary Examiner*—Nicholas D Lucchesi
*Assistant Examiner*—Theodore J Stigell
(74) *Attorney, Agent, or Firm*—Panitch Schwarze Belisario & Nadel LLP

(57) ABSTRACT

A coupling for selectively securing a spring to a plunger is provided. The coupling has a first end defining a spring rest for receiving the spring and a second end defining a shoulder. The shoulder is moveable to a first position into contact with the plunger and to a second position out of contact with the plunger. The shoulder is normally in the second position and is resiliently moveable to the first position.

8 Claims, 8 Drawing Sheets

U.S. PATENT DOCUMENTS

| | | |
|---|---|---|
| 4,689,042 A | 8/1987 | Sarnoff et al. |
| 4,755,169 A | 7/1988 | Sarnoff et al. |
| 4,767,413 A | 8/1988 | Haber et al. |
| 4,795,444 A | 1/1989 | Hasegawa et al. |
| 4,820,286 A | 4/1989 | Van Der Wal |
| 4,822,340 A | 4/1989 | Kamstra |
| 4,861,335 A | 8/1989 | Reynolds |
| 4,886,495 A | 12/1989 | Reynolds |
| 4,898,580 A | 2/1990 | Crowley |
| 4,969,877 A | 11/1990 | Kornberg |
| 4,998,922 A | 3/1991 | Kuracina et al. |
| 5,045,058 A | 9/1991 | Demetrakopoulos |
| 5,049,133 A | 9/1991 | Villen Pascual |
| 5,085,641 A | 2/1992 | Sarnoff et al. |
| 5,085,642 A | 2/1992 | Sarnoff et al. |
| 5,092,843 A | 3/1992 | Monroe et al. |
| 5,102,393 A | 4/1992 | Sarnoff et al. |
| 5,120,310 A | 6/1992 | Shaw |
| 5,137,511 A | 8/1992 | Reynolds |
| 5,169,385 A | 12/1992 | Turnbull |
| 5,176,657 A | 1/1993 | Shields |
| 5,188,613 A | 2/1993 | Shaw |
| D339,606 S | 9/1993 | Podobrin |
| 5,267,961 A | 12/1993 | Shaw |
| 5,295,965 A | 3/1994 | Wilmot |
| 5,300,030 A * | 4/1994 | Crossman et al. ........... 604/136 |
| 5,324,273 A | 6/1994 | Discko, Jr. |
| 5,358,489 A | 10/1994 | Wyrick |
| 5,364,363 A | 11/1994 | Pearson et al. |
| 5,383,865 A | 1/1995 | Michel |
| 5,385,551 A | 1/1995 | Shaw |
| 5,389,076 A | 2/1995 | Shaw |
| 5,391,151 A | 2/1995 | Wilmot |
| 5,411,487 A | 5/1995 | Castagna |
| 5,411,489 A | 5/1995 | Pagay et al. |
| 5,413,564 A | 5/1995 | Silver et al. |
| 5,423,758 A | 6/1995 | Shaw |
| 5,425,715 A | 6/1995 | Dalling et al. |
| 5,466,223 A * | 11/1995 | Bressler et al. ............. 604/110 |
| 5,531,255 A | 7/1996 | Vacca |
| 5,540,664 A | 7/1996 | Wyrick |
| 5,545,145 A | 8/1996 | Clinton et al. |
| 5,578,011 A | 11/1996 | Shaw |
| 5,599,309 A | 2/1997 | Marshall |
| 5,620,421 A | 4/1997 | Schmitz |
| 5,632,733 A | 5/1997 | Shaw |
| 5,637,092 A | 6/1997 | Shaw |
| 5,643,214 A * | 7/1997 | Marshall et al. ............. 604/134 |
| 5,665,071 A | 9/1997 | Wyrick |
| 5,674,204 A | 10/1997 | Chanoch |
| 5,685,846 A | 11/1997 | Michaels, Jr. |
| 5,688,251 A | 11/1997 | Chanoch |
| 5,695,472 A | 12/1997 | Wyrick |
| 5,779,677 A | 7/1998 | Frezza |
| 5,779,679 A * | 7/1998 | Shaw ......................... 604/158 |
| 5,810,775 A | 9/1998 | Shaw |
| 5,817,058 A | 10/1998 | Shaw |
| RE35,986 E | 12/1998 | Ritson et al. |
| 5,860,961 A | 1/1999 | Gettig |
| 5,873,462 A | 2/1999 | Nguyen et al. |
| 5,921,966 A | 7/1999 | Bendek et al. |
| 5,931,817 A | 8/1999 | Nguyen et al. |
| 5,941,857 A | 8/1999 | Nguyen et al. |
| 5,944,700 A | 8/1999 | Nguyen et al. |
| D414,201 S | 9/1999 | Larson et al. |
| 5,957,896 A | 9/1999 | Bendek et al. |
| 5,957,897 A | 9/1999 | Jeffrey |
| D414,807 S | 10/1999 | Baudino et al. |
| 5,961,495 A | 10/1999 | Walters et al. |
| 5,989,220 A | 11/1999 | Shaw et al. |
| 5,997,512 A | 12/1999 | Shaw |
| 6,001,082 A | 12/1999 | Dair et al. |
| 6,015,438 A | 1/2000 | Shaw |
| D423,577 S | 4/2000 | Baudino et al. |
| D425,120 S | 5/2000 | Ramil |
| 6,086,563 A | 7/2000 | Moulton et al. |
| 6,095,814 A | 8/2000 | Petrich et al. |
| 6,099,503 A | 8/2000 | Stradella |
| 6,149,623 A | 11/2000 | Reynolds |
| 6,183,445 B1 | 2/2001 | Lund et al. |
| 6,200,627 B1 | 3/2001 | Lubrecht |
| 6,210,315 B1 | 4/2001 | Andrews et al. |
| 6,210,369 B1 | 4/2001 | Wilmot et al. |
| 6,210,371 B1 | 4/2001 | Shaw et al. |
| 6,213,597 B1 | 4/2001 | Liu |
| 6,221,046 B1 | 4/2001 | Burroughs et al. |
| 6,221,053 B1 | 4/2001 | Walters et al. |
| 6,221,055 B1 | 4/2001 | Shaw et al. |
| D441,398 S | 5/2001 | Owen et al. |
| 6,248,095 B1 | 6/2001 | Giambattista et al. |
| D446,242 S | 8/2001 | Stukenkemper |
| 6,277,099 B1 | 8/2001 | Strowe et al. |
| D452,271 S | 12/2001 | Owen et al. |
| 6,328,715 B1 | 12/2001 | Dragan et al. |
| 6,346,094 B2 | 2/2002 | West et al. |
| 6,349,850 B1 | 2/2002 | Cheikh |
| 6,387,078 B1 * | 5/2002 | Gillespie, III ............... 604/181 |
| 6,494,863 B1 | 12/2002 | Shaw et al. |
| 6,572,584 B1 | 6/2003 | Shaw et al. |
| 6,638,244 B1 | 10/2003 | Reynolds |
| 6,689,118 B2 | 2/2004 | Alchas et al. |
| 6,793,646 B1 | 9/2004 | Giambattista et al. |
| 6,796,967 B2 | 9/2004 | Jensen |
| 6,802,828 B2 | 10/2004 | Reynolds |
| 2001/0002434 A1 | 5/2001 | Lubrecht |
| 2001/0029354 A1 | 10/2001 | Rolle et al. |
| 2001/0039400 A1 | 11/2001 | Lubrecht |
| 2002/0010430 A1 | 1/2002 | Dragan et al. |
| 2002/0164265 A1 | 11/2002 | Hetzler |
| 2002/0177819 A1 | 11/2002 | Barker et al. |
| 2003/0083621 A1 | 5/2003 | Shaw et al. |
| 2003/0088216 A1 | 5/2003 | Py |
| 2003/0100866 A1 | 5/2003 | Reynolds |
| 2003/0130626 A1 | 7/2003 | VanTassel et al. |
| 2003/0187388 A1 | 10/2003 | Sharon et al. |
| 2004/0024367 A1 | 2/2004 | Gilbert |
| 2004/0111064 A1 | 6/2004 | Asbaghi |
| 2005/0049551 A1 | 3/2005 | Kirchhofer |
| 2005/0113763 A1 | 5/2005 | Reynolds |
| 2006/0178629 A1* | 8/2006 | Gillespie et al. ............. 604/134 |
| 2006/0178631 A1 | 8/2006 | Gillespie et al. |

FOREIGN PATENT DOCUMENTS

| | | |
|---|---|---|
| JP | 10057483 A | 3/1998 |
| WO | 2006063124 A2 | 6/2006 |

OTHER PUBLICATIONS

International Search Report and Written Opinion for related International Patent Application No. PCT/US05/44492; dated May 25, 2006.

International Search Report and Written Opinion for the corresponding International Patent Application No. PCT/US05/44410; dated Jun. 27, 2006.

International Search Report for related International Patent Application No. PCT/US06/27733; dated Apr. 23, 2007.

International Preliminary Report on Patentability for related International Patent Application No. PCT/US05/44411; dated Jun. 8, 2008.

International Search Report and Written Opinion for related International Patent Application No. PCT/US05/44411; dated Jun. 21, 2007.

Chinese Office Action for related Chinese Patent Application No. 200580047001.0; dated Jul. 17, 2009.

A First Office Action for related Chinese Patent Application No. 200580047294.2; mailed Aug. 21, 2009; 7 pages (English translation only).

Office Action for the related U.S. Appl. No. 11/296,973 issued Apr. 17, 2009.

Office Action for the related U.S. Appl. No. 11/297,159 issued Mar. 29, 2006.

Office Action for the related U.S. Appl. No. 11/297,159 issued Apr. 11, 2007.

Office Action for the related U.S. Appl. No. 11/297,159 issued Dec. 31, 2007.

Office Action for the related U.S. Appl. No. 11/297,159 issued Nov. 13, 2008.

International Preliminary Report on Patentability for the related International Application No. PCT/US05/44410 dated Jan. 17, 2007.

Examination Report and Written Opinion for the related Singapore Application No. 200704199-9 issued Jun. 27, 2008.

Examination Report for the related Singapore Application No. 200704201-3 issued Jul. 7, 2009.

Office Action for the related U.S. Appl. No. 11/458,114 dated Apr. 28, 2010.

Chinese Office Action for the related Chinese Application No. 200680026185.7 dated Mar. 1, 2010.

\* cited by examiner

US 7,758,548 B2

COUPLING FOR AN AUTO-INJECTION DEVICE

CROSS REFERENCE TO RELATED APPLICATIONS

This application claims priority of U.S. Provisional Application Ser. No. 60/634,486 filed on Dec. 9, 2004 and is related to commonly owned and assigned U.S. application Ser. No. 10/601,212, filed Jun. 20, 2003, the contents of both of which are incorporated by reference herein.

BACKGROUND OF THE INVENTION

1. Field of the Invention

The present disclosure is related to auto-injection devices. More particularly, the present disclosure is related to a coupling for auto-injection devices for releasably securing an injection spring to a plunger rod.

2. Description of Related Art

Diseases such as AIDS, Hepatitis, and others, are increasing within the general population. The onset of these diseases has increased the desire to prevent inadvertent needle sticks during the use of syringe assemblies. Many prior art devices include self-retracting needles to mitigate inadvertent needle sticks.

Many life-threatening situations such as allergy induced anaphylactic shock, and exposure to chemical, radiological, and biological weapons can require the use of automatic injection devices. Also, many non-threatening conditions can be candidates for use of such automatic injection devices. However, the cost of the prior art automatic injection device can make such use by consumers cost prohibitive.

Typical automatic injection devices are syringe assemblies that allow the medically untrained user to automatically inject a medicine by manually trigging the automatic injection. Some prior automatic injection devices also incorporate self-retracting needles. Such automatic injection and retraction assemblies included a coupling that releasably couples an injection spring to a syringe plunger. Unfortunately, many prior couplings require tight manufacturing tolerances, which can increase the overall cost of the device.

Accordingly, there is a continuing need for auto-injection devices and couplings for such devices that overcome and/or mitigate one or more of the aforementioned and other deficiencies and deleterious effects of prior automatic injection devices.

BRIEF SUMMARY OF THE INVENTION

It is an object of the present disclosure to provide a coupling for selectively securing a spring to a plunger. The coupling has a first end defining a spring rest for receiving the spring and a second end defining a shoulder. The shoulder is moveable to a first position into contact with the plunger and to a second position out of contact with the plunger. The shoulder is normally in the second position and is resiliently moveable to the first position.

In some embodiments, the coupling includes a first end defining a spring rest for receiving the spring and a second end defining a shoulder. The spring rest and the shoulder are radially offset from one another by a predetermined angle.

In other embodiments, the coupling includes a first end defining a pair of spring rests for receiving the spring and a second end defining a pair of shoulders. The pair of shoulders are moveable to a first position into contact with the plunger and a second position out of contact with the plunger.

A power injection assembly is also provided. The assembly includes a plunger rod, an injection spring, an inner housing, and a coupling. The plunger rod has a rib. The inner housing has a first opening and an inner diameter. The injection spring is about the inner housing and the plunger rod is in the inner diameter. The coupling has a spring rest and a shoulder. The coupling is in the inner diameter such that the spring rest extends through the first opening and receives the injection spring and such that the shoulder is compressed to a first position by the inner diameter. The shoulder is engaged with the rib in the first position.

The above-described and other features and advantages of the present disclosure will be appreciated and understood by those skilled in the art from the following detailed description, drawings, and appended claims.

DETAILED DESCRIPTION OF THE INVENTION

Figure 1:
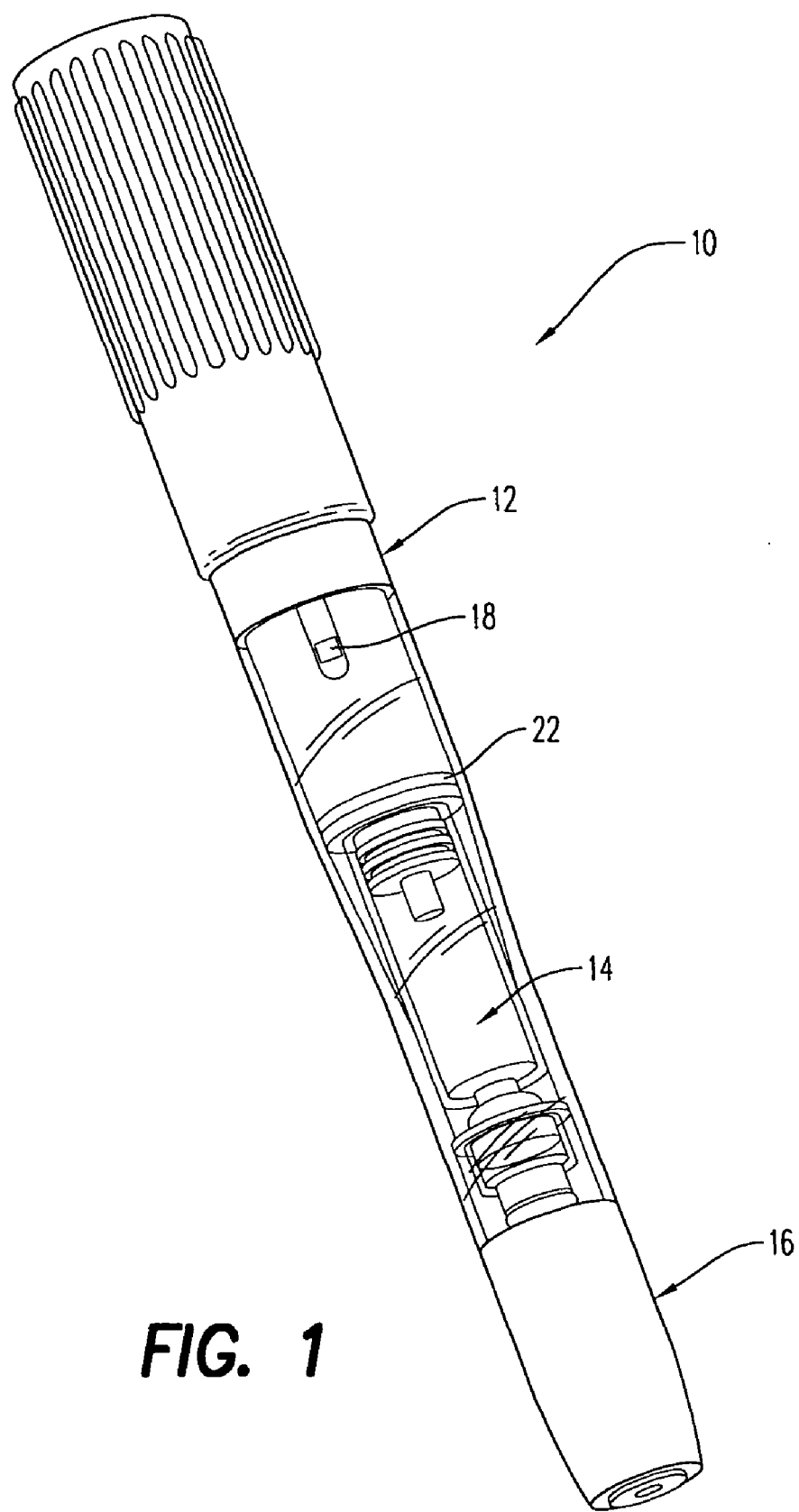
FIG. 1 is a perspective view of an exemplary embodiment of an auto-injection device according to the present disclosure.
Figure 2:
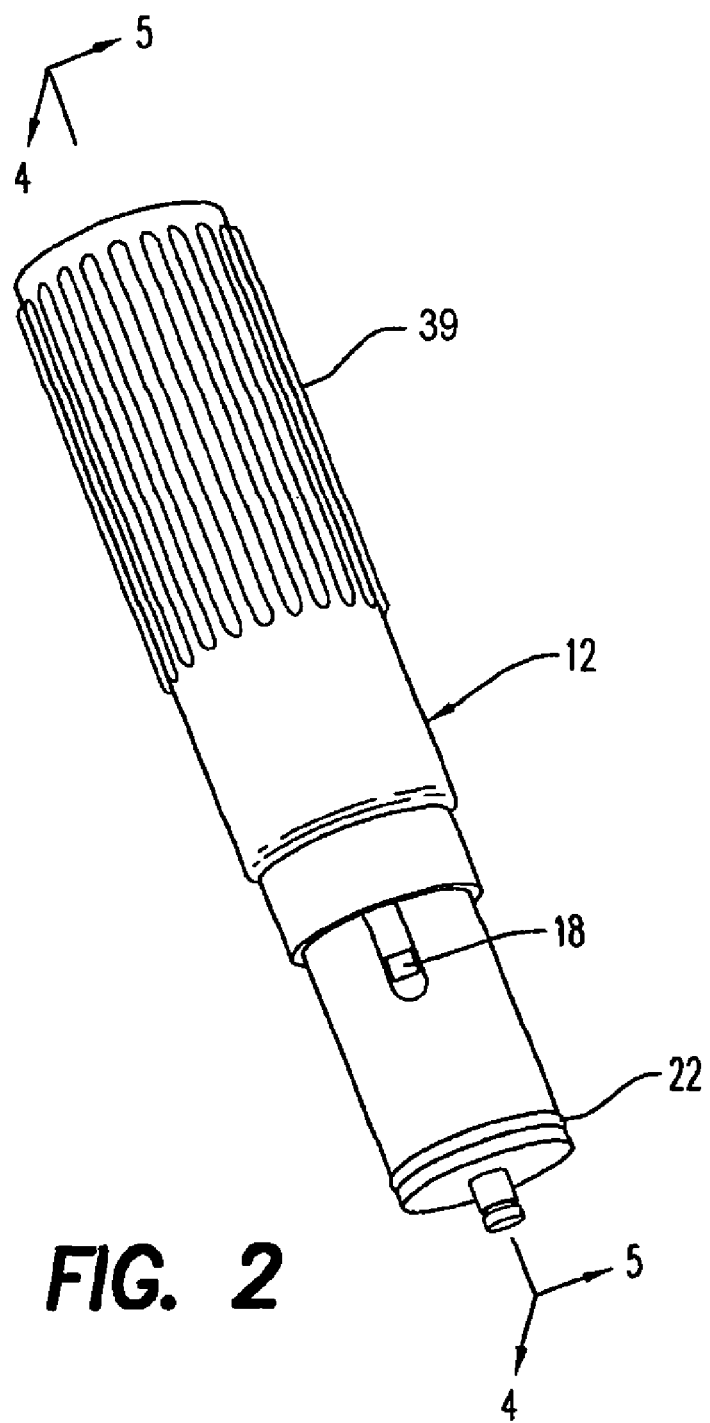
FIG. 2 is a perspective view of a power-injection assembly of FIG. 1 shown before assembly.
Figure 3:
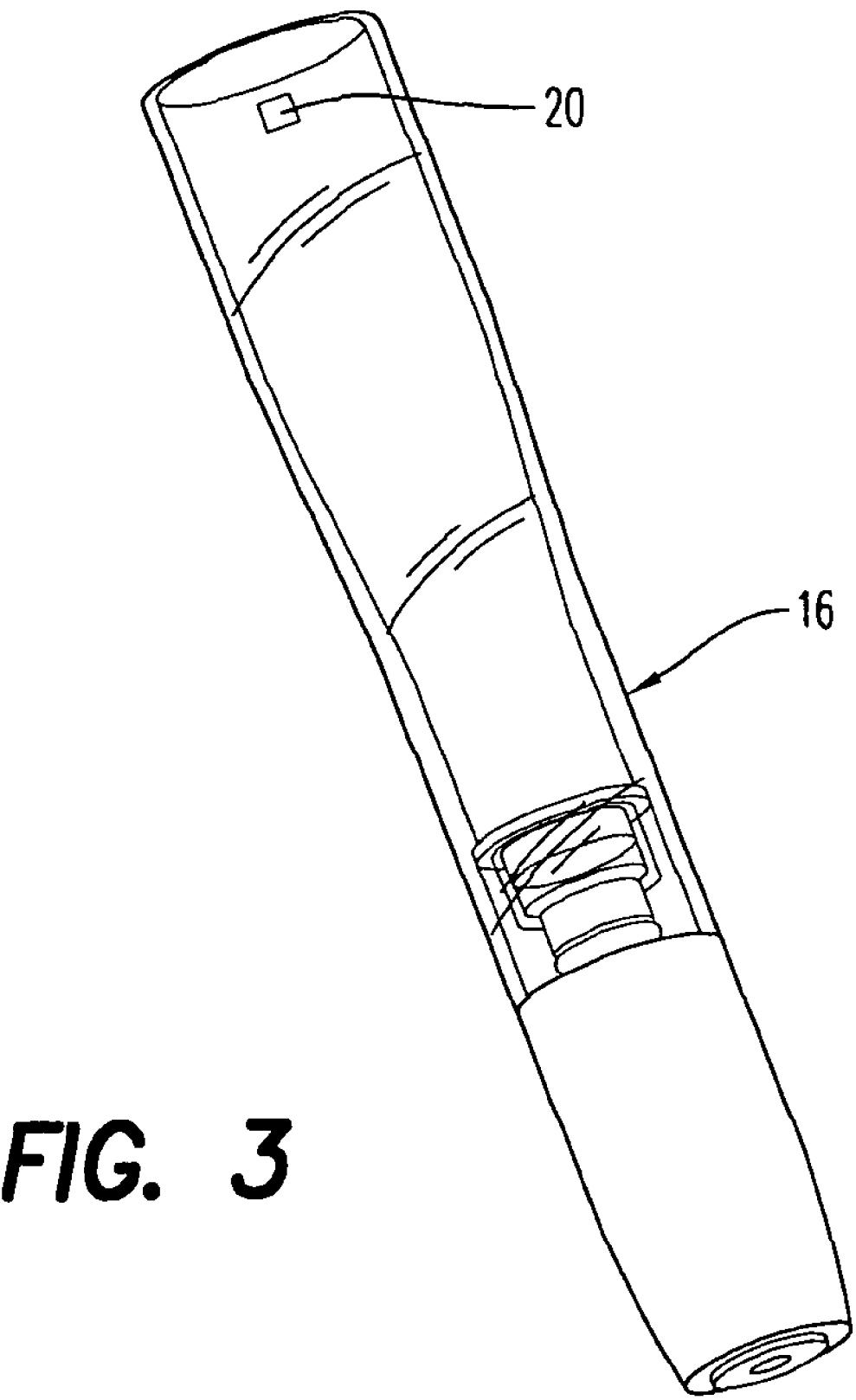
FIG. 3 is a perspective view of a power-retraction assembly of FIG. 1 shown before assembly.

Referring to the figures and in particular to FIGS. 1 through 3, an exemplary embodiment of an auto-injection device 10 according to the present disclosure is shown in an assembled state. Auto-injection device 10 includes a power-injection assembly 12, a medicine cartridge 14, and a power-retraction assembly 16.

Auto-injection device 10 is configured to extend a hypodermic needle from within the device, inject a single, pre-measured dose of medicine from cartridge 14 into a user, and automatically retract the hypodermic needle into the device after the injection is completed.

Advantageously, syringe assembly 10 is a multi-component device that can be assembled by the user and/or medical provided (e.g., pharmacist, doctor, nurse). Since syringe assembly 10 does not require assembly at the time of manufacture, the present disclosure effectively separates expiry of medicine cartridge 14 from the expiry of syringe assembly 10. For example, typical flu vaccines have an expiration date of one year. Thus, the user can maintain a supply of power injection and retraction assemblies 12, 16 of the present disclosure, while only replacing any expired medicine cartridges 14.

For example, power-injection assembly 12 and power-retraction assembly 16 can be secured to one another in a snap fit manner so that the assemblies can not be removed from one another after injection. In the illustrated embodiment, power-injection assembly 12 includes one or more outwardly depending tabs 18 that are received in a corresponding number of openings 20 defined in power-retraction assembly 16. As power-injection assembly 12 is inserted into power-retraction assembly 16, tabs 18 act on the power-retraction assembly to elastically deform the inner dimension of the tube. Once tabs 18 are received by openings 20, the inner dimension of power-retraction assembly 16 resiliently returns to its original dimension to secure the tabs in the openings.

In the assembled state, syringe assembly 10 preferably maintains cartridge 14 hermetically sealed between power-injection and retraction assemblies 12, 16. For example, power-injection assembly 12 can include a sealing member 22 such as, but not limited to an o-ring. Once power-injection assembly 12 and power-retraction assembly 16 are secured together, sealing member 22 cooperates with the interior of the power-retraction assembly to form a hermetic radial seal. In the illustrated embodiment, sealing member 22 is positioned below openings 20 defined in power-retraction assembly 16 to provide the hermetic seal below the snap fit connection between tabs 18 and openings 20.

Figure 6:
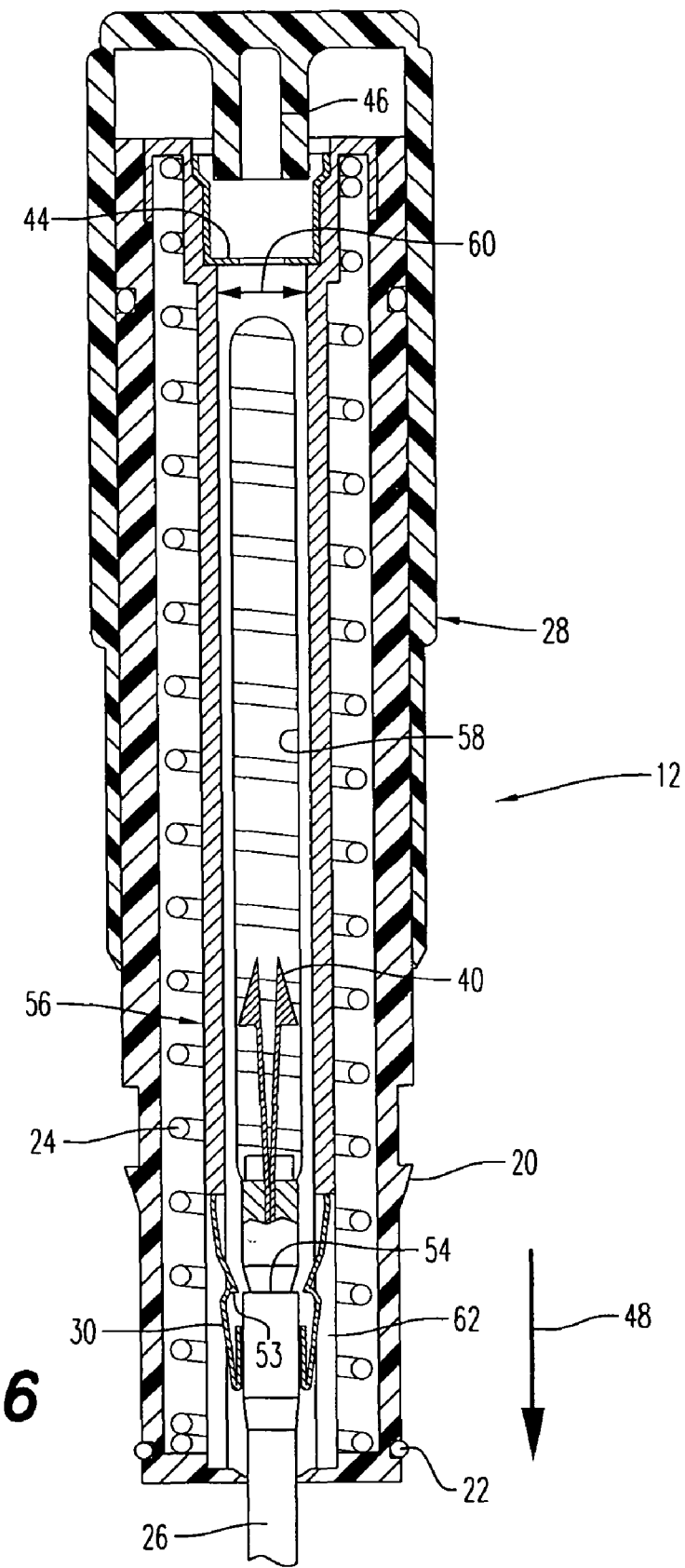
FIG. 6 is a view of the power-injection assembly of FIG. 5 shown after activation.
Figure 7:
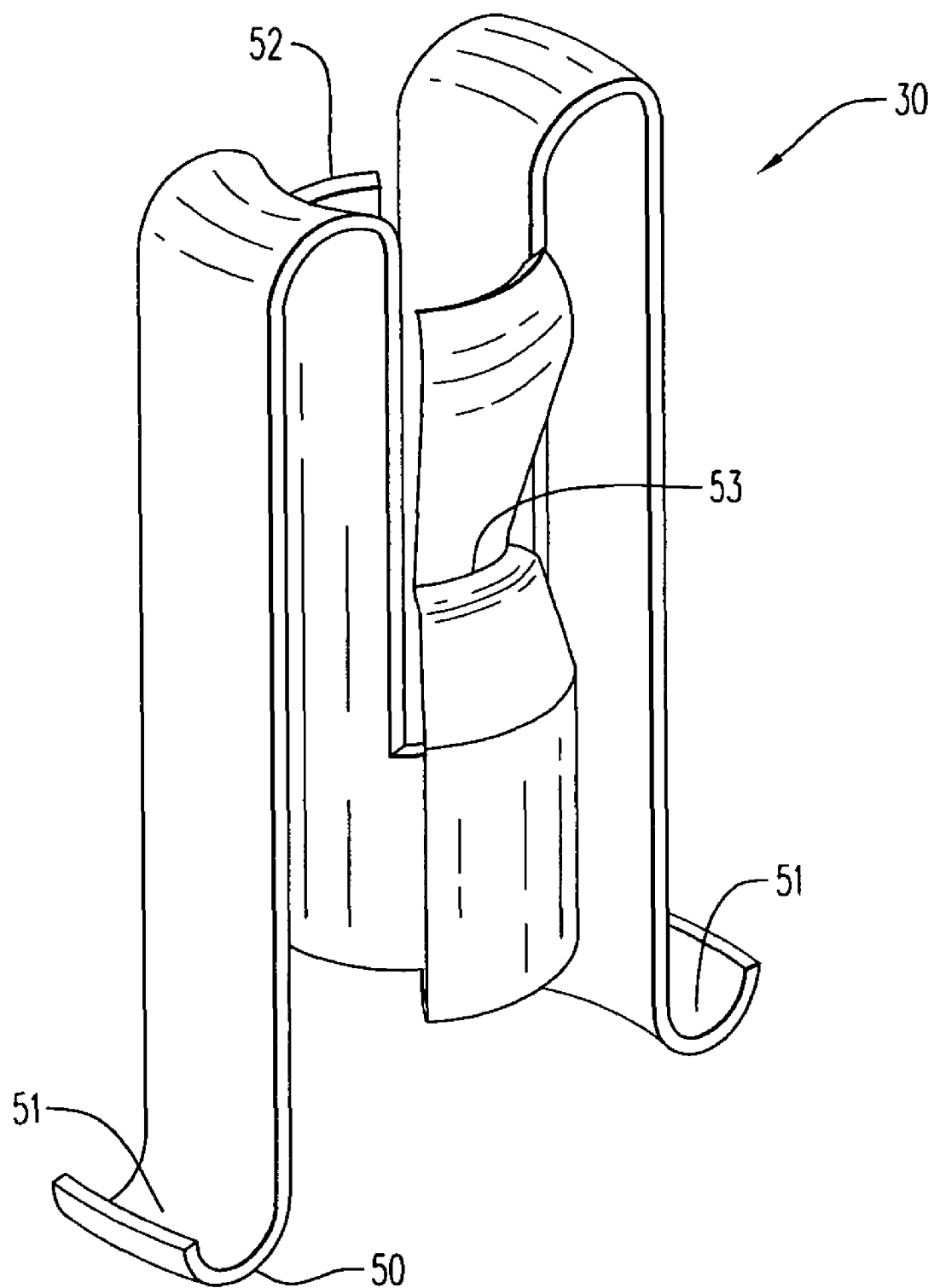
FIG. 7 is a perspective view of an exemplary embodiment of a metal spring to plunger coupling according to the present disclosure.

The operation of the power-injection assembly 12 is described with simultaneous reference to FIGS. 4 through 8. Injection assembly 12 includes an injection spring 24, a plunger rod 26, an activation device 28, a coupling 30, and a housing 11 that houses the spring 24, plunger rod 26, coupling 30, and inner housing 56 (FIG. 7). Injection spring 24 is disposed about plunger rod 26 and is drivingly engaged to the plunger rod by coupling 30.

Activation device 28 has an upper end 32 and a lower end 34. Injection assembly 12 is activated by depressing activation device 28 in direction 48. In addition, activation device 28 can include an outer shroud 36. Outer shroud 36 and injection assembly 12 can include one or more cooperating guides (not shown) that permit depression of activation device 28 only after the activation device has been rotated to a predetermined position. In sum, outer shroud 36 and injection assembly 12 can work together to require movement in two directions, rotation and depression, in order to activate injection spring 24. In a preferred embodiment, shroud 36 includes a number of longitudinal ribs 39 to assist the user in rotation. In this manner, injection assembly 12 is particularly suited for use in situations where the user may lack typical manual dexterity, such as can be the case where the user is wherein protective gloves.

Lower end 34 is configured to selectively couple the energy from injection spring 24 to drive plunger rod 26. In the illustrated embodiment, plunger rod 26 includes a driving end 38 and a locking end 40. Locking end 40 includes two tines 42 that are resiliently biased outward so that the tines are remote from one another. Driving end 38 is configured to act on medicine cartridge 14 in a known manner. For example, driving end 38 can act on medicine cartridge 14 as described in U.S. Pat. No. 6,387,078.

Injection assembly 12 includes a locking member 44 that engages tines 42 when the tines are normally biased from one another. Activation device 28 includes a releasing surface 46 defined at lower end 34. Force applied to upper end 32 of activation device 28 in direction 48 causes releasing surface 46 to compress tines 42 toward one another such that the tines are disengaged from locking member 44.

Injection spring 24 is maintained in a normally compressed or stressed condition. Upon release of tines 42 from locking member 44, the stored energy in spring 24 drives plunger rod 26 in an injection direction 48.

Figure 4:
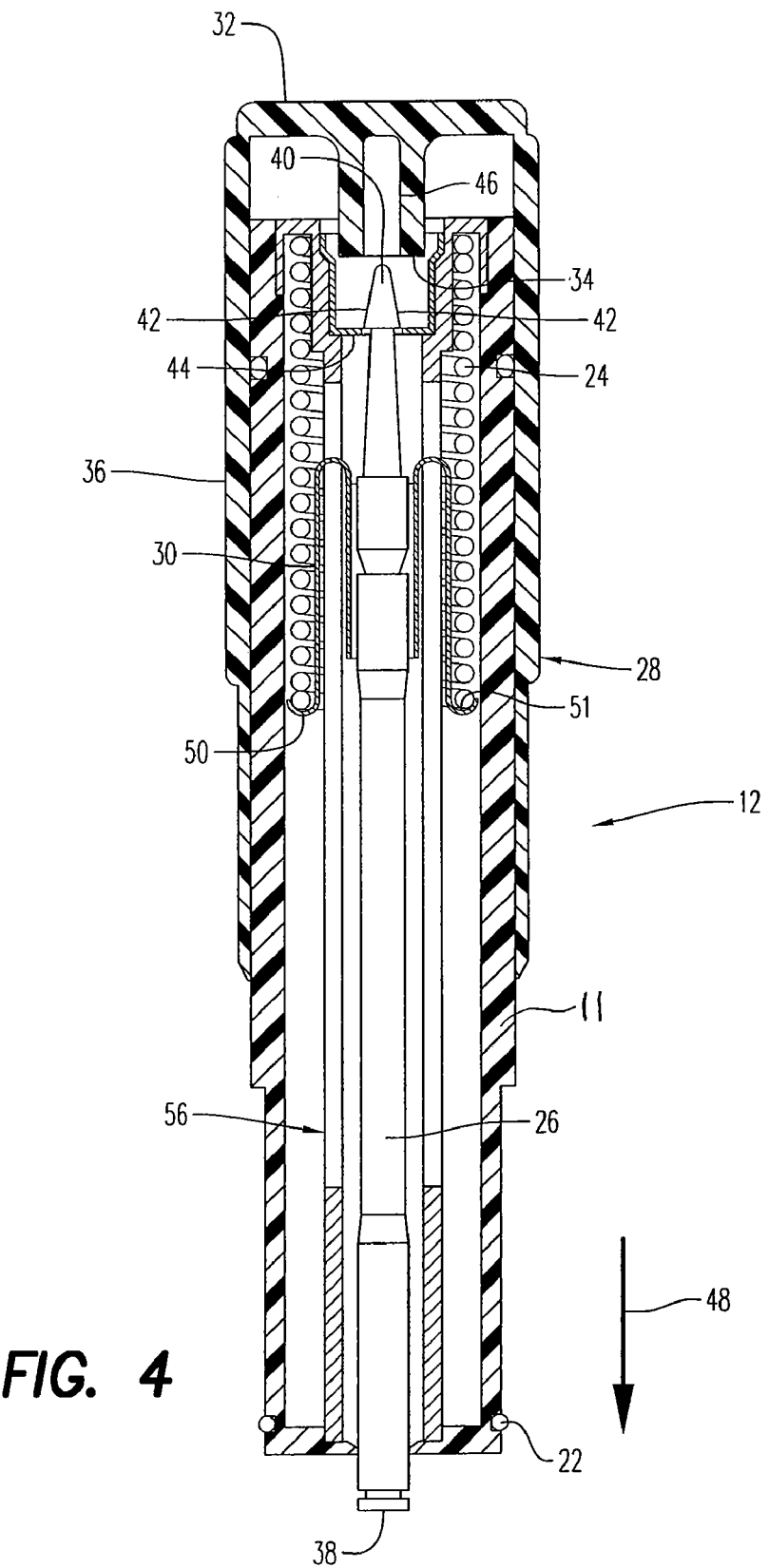
FIG. 4 is a first cross sectional view of the power-injection assembly of FIG. 2 taken along lines 4-4.
Figure 5:
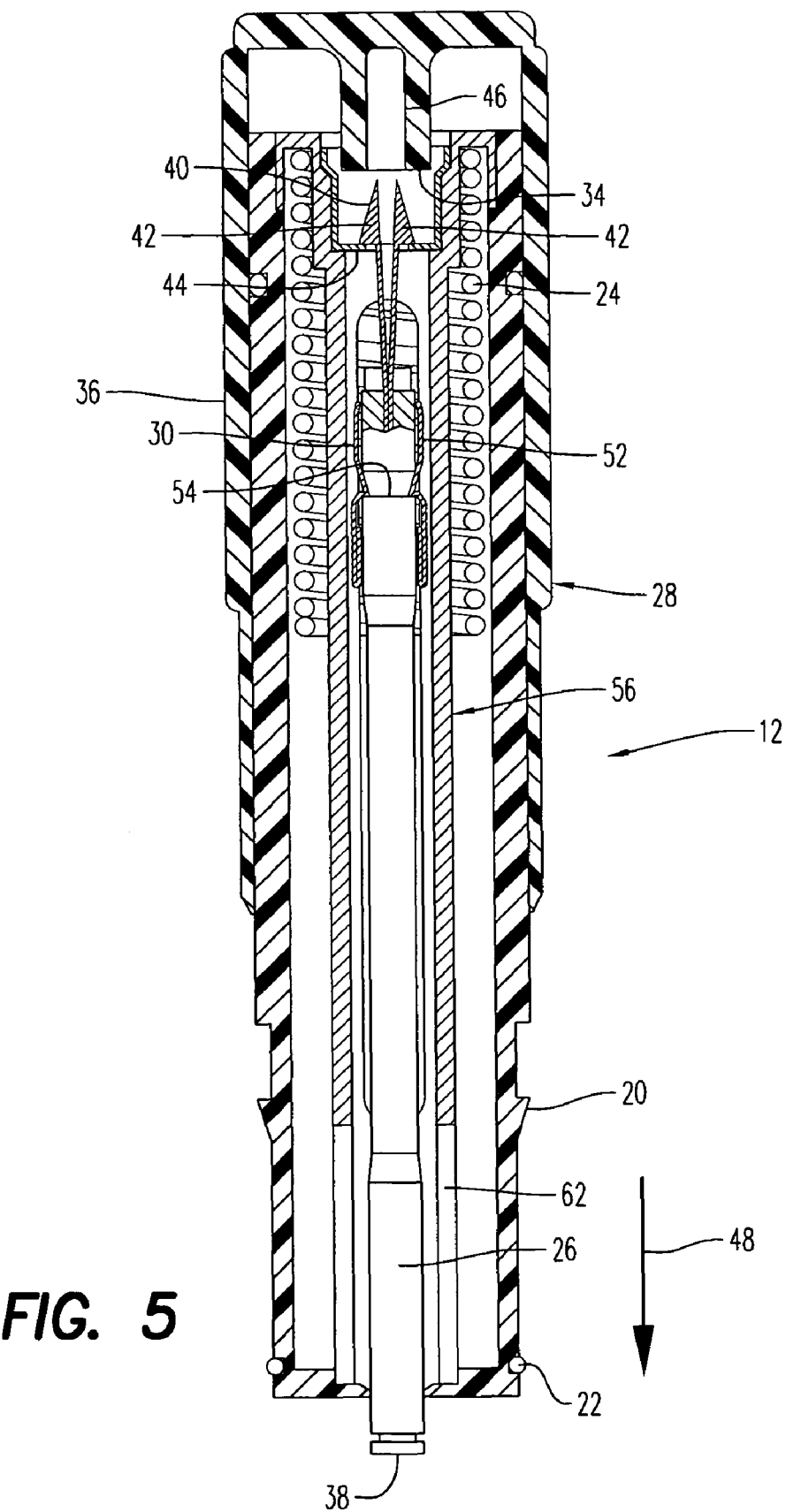
FIG. 5 is a second cross sectional view of the power-injection assembly of FIG. 2 taken along lines 5-5.

Coupling 30 includes a first end 50 and a second end 52. First end 50 forms a spring rest or seat 51 upon which injection spring 24 rests as shown in FIG. 4.

Second end 52 (shown in FIGS. 5 and 6) is an outwardly biased spring member having a shoulder 53 for engaging plunger rod 26. During assembly, second end 52 is compressed inward towards plunger rod 26 until shoulder 53 engages a rib 54 defined on plunger rod. Thus, second end 52 is moveable between a compressed or first position (FIG. 5) and a normal or second position (FIG. 6). Second end 52 is normally in the second position, but has sufficient resiliency such that the second end can be elastically urged to the first position.

During movement of plunger rod 26 in injection direction 48, second end 52 is maintained in the compressed position and, thus, shoulder 53 is maintained engaged with rib 54 so that the force of injection spring 24 is transmitted through coupling 30 to plunger rod 26.

After plunger rod 26 has traveled a predetermined distance, second end 52 is allowed to bias outward away from rod 26 so that shoulder 53 disengages from rib 54 as shown in FIG. 6. Thus, second end 52 moves from the compressed position to the normal position due to its own resiliency once plunger rod 26 travels the predetermined distance to disengage shoulder 53 from rib 54. Once shoulder 53 is disengaged from rib 54, the force of injection spring 24 is no longer transmitted through coupling 30 to plunger rod 26.

Preferably, coupling 30 includes a pair of spring rests 51 and a pair of shoulders 53. Here, spring rests 51 are, preferably, diametrically opposed to one another. Similarly, shoulders 53 are, preferably, diametrically opposed to one another. Moreover, spring rests 51 are, preferably, radially offset from shoulders 53 and circumferentially offset from the shoulder 53 by a predetermined angle, preferably about 90 degrees. In this manner, each spring rest 51 is circumferentially offset from each shoulder 53 by about by about 90 degrees.

Spring rests 51 are, preferably, axially offset from shoulders 53 by a predetermined distance so that coupling 30 has an axial length. In this manner, spring rests 51 are disposed forward relative to shoulders 53 along the axial length so that spring 24 encompasses a portion of the axial length.

For applications involving auto-injection devices 10 for small dose volumes deposited at shallow depths, the demand on injection spring 24, in terms of the spring rate and extension length, are not very severe. Thus, injection spring 24 can be incorporated into power-injection assembly 12 with a reasonable set of device proportions (e.g., length and diameter). However, in cases with auto-injection devices 10 that must deliver larger dose volumes deposited at deeper needle penetration depths, the demand on injection spring 24, in terms of the spring rate and extension length, can be severe. In these applications, injection spring 24 requires a long travel and high spring rate. This combination of high spring rate and long travel typically requires injection spring 24 to be a long, slender spring positioned in straight line sequence with the plunger, which unfortunately leads to power-injection assembly 12 having an undesireably long length. Alternately, the combination of high spring rate and long travel typically requires injection spring 24 to have a large diameter.

Advantageously, coupling 30 is particularly suited for use with such large diameter springs. Specifically, coupling 30 has spring rests 51 that are disposed radially outward from the coupling and are disposed forward of shoulders 53. In this manner, injection spring 24 encompasses a portion of the axial length of coupling 30 so that the larger diameter spring axially overlaps at least a portion of plunger rod 26. According, coupling 30 finds particular use with large diameter springs to mitigate the overall length of power-injection assembly 12.

Figure 8:
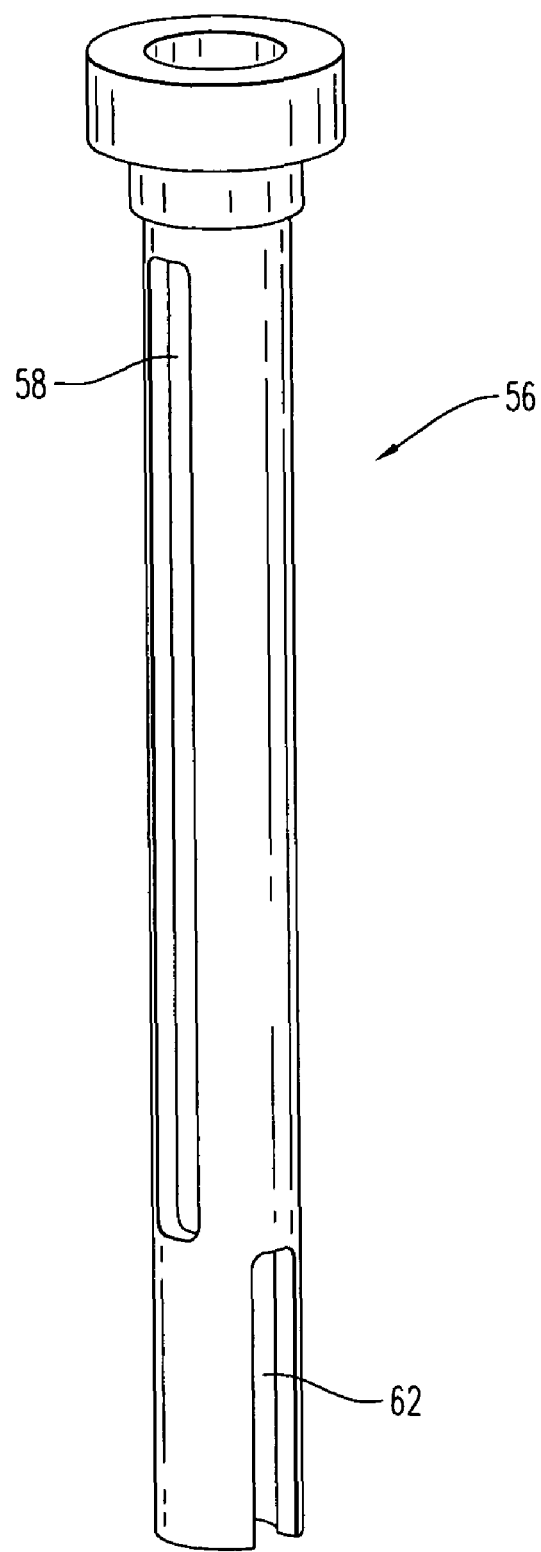
FIG. 8 is a perspective view of an exemplary embodiment of an inner housing according to the present disclosure.

In the illustrated embodiment, injection assembly 12 includes an inner housing 56 shown in FIG. 8. Inner housing 56 defines has a first opening 58 through which spring rest 51 extends to engage injection spring 24. First opening 58 extends along inner housing 56 in the injection direction 48. Preferably, inner housing 56 has a pair of first openings 58 that are defined through the inner housing diametrically opposed to one another to receive a pair of diametrically opposed spring rests 51.

Inner housing 56 has an inner diameter 60 that is sufficient to maintain second end 52 of coupling 30 in the compressed position and, thus, engaged with plunger rod 26. Thus, second end 52 is outwardly biased against inner diameter 60 of inner housing 56. The force of injection spring 24 is sufficient to overcome the friction between second end 52 and housing 56.

Inner housing 56 also includes a second opening 62. Preferably, inner housing 56 has a pair of second openings 62 that are defined through the inner housing diametrically opposed to one another. Second opening 62 is offset from first opening 58 by the same predetermined angle that offsets spring rest 51 from shoulder 53. Thus, second opening 62 is aligned with shoulder 53 of coupling 30.

Second opening 62 is defined at a predefined position along injection direction 48 where it is desired for coupling 30 to disengage injection spring 24. Thus, after plunger rod 26 has traveled to the point where second end 52 of coupling 30 is at second opening 62, the second end 52 is no longer maintained in the compressed position by inner diameter 60, which allows the second end to resiliently bias outward to the first position through the second opening and move shoulder 53 out of engagement with rib 54.

Advantageously, coupling 30 can be made of any material having sufficient resiliency to bias second end 52 outward at second opening 62. For example, coupling 30 can be made of spring steel stamped into the desired shape such as that illustrated in FIG. 7. Accordingly, coupling 30 can be made less expensively and with lower manufacturing tolerances than previous couplings.

In this manner, injection spring 24 drives plunger rod 26 in injection direction 48 until second end 52 of coupling 30 reaches second opening 52. The resiliency of coupling 30 causes the coupling to expand through second opening 52 and disengage shoulder 53 from rib 54 of plunger rod 26 as seen in FIG. 6. The disengagement of coupling 30 from plunger rod 26 frees the plunger rod from the force of injection spring 24 and, thus, allows the plunger rod to be moved in a direction opposite injection direction 48 by retraction assembly 16.

Retraction assembly 16 can operate in a known manner. For example, power-retraction assembly 16 can include a retraction spring (not shown) that has a spring force lower than the spring force of injection spring 24. Thus, injection spring 24 overcomes the force of the retraction spring as long as coupling 30 engages plunger rod 26 to the injection spring. However, once second end 52 of coupling 30 is disengaged from plunger rod 26 and the force of injection spring 24 is no longer transmitted through the coupling to the plunger rod, the force of the retraction spring is sufficient to urge medicine cartridge 14 in a direction opposite injection direction 48, thus automatically retracting the hypodermic needle of cartridge 14 into device 10.

It should be noted that the terms "first", "second", "third", "upper", "lower", and the like may be used herein to modify various elements. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

The invention claimed is:

1. A power injection assembly, comprising:
   a plunger rod having a rib;
   an injection spring;
   an inner housing having a first opening and an inner diameter, said injection spring surrounding said inner housing and said plunger rod being disposed in said inner diameter; and
   a coupling having a spring rest and a shoulder, said coupling being disposed in said inner diameter such that said spring rest extends through said first opening and receives said injection spring and such that said shoulder is compressed to a first position by said inner diameter, said shoulder being engaged with said rib in said first position.

2. The assembly of claim 1, wherein said inner housing further comprises a second opening defined at a predetermined position along an injection direction.

3. The assembly of claim 2, wherein said second opening allows said shoulder to resiliently bias through said inner housing to a second position, said shoulder being disengaged from said rib in said second position.

4. The assembly of claim 2, wherein said injection spring acts on said coupling to urge said plunger in said injection direction.

5. The assembly of claim 2, further comprising an activation device said activation device maintaining said injection spring in a compressed state, said shoulder being remote from said second opening in said compressed state.

6. The assembly of claim 5, wherein said activation device releases said injection spring from said compressed state upon movement of said activation device in two directions.

7. The assembly of claim 1, wherein said spring rest is radially offset and axially offset relative to said shoulder.

8. The assembly of claim 1, further comprising a housing that houses the plunger rod, the injection spring, the inner housing and the coupling.

* * * * *